United States Patent [19]

Bargiotti et al.

[11] 4,366,149

[45] Dec. 28, 1982

[54] ANTITUMOR ANTHRACYCLINE GLYCOSIDES, THEIR PREPARATION, INTERMEDIATES THEREFOR, AND COMPOSITIONS AND USE THEREOF

[76] Inventors: Alberto Bargiotti, Via Donati, 8, Milan; Giuseppe Cassinelli, Via G. Matteotti, 13, Voghera (Pavia); Sergio Penco, Via Crimea, 13, Milan; Federico Arcamone, Via 4 Novembre, 26, Nerviano (Milan); Annamaria Casazza, Via Guido Reni, 26, Milan, all of Italy

[21] Appl. No.: 316,057

[22] Filed: Oct. 29, 1981

[30] Foreign Application Priority Data

Nov. 1, 1980 [GB] United Kingdom ............... 8035204

[51] Int. Cl.³ .................... A61K 31/70; C07H 5/06; C07H 15/24

[52] U.S. Cl. .................... 424/180; 536/6.4; 536/53; 536/122

[58] Field of Search ............ 536/17 A, 53, 122; 424/180

[56] References Cited

U.S. PATENT DOCUMENTS

| | | | |
|---|---|---|---|
| 4,020,270 | 4/1977 | Arcamone et al. | 536/17 A |
| 4,039,663 | 8/1977 | Arcamone et al. | 536/122 |
| 4,067,969 | 1/1978 | Penco et al. | 536/122 |
| 4,265,885 | 5/1981 | Bargiotti et al. | 536/53 |

*Primary Examiner*—Johnnie R. Brown

[57] ABSTRACT

Novel antitumor anthracycline glycosides are prepared by condensing daunomycinone with 2,3,4,6-tetradeoxy-3,4-ditrifluoroacetamido-L-lyxo-[or L-arabino-]hexopyranosyl chloride.

10 Claims, No Drawings

ANTITUMOR ANTHRACYCLINE GLYCOSIDES, THEIR PREPARATION, INTERMEDIATES THEREFOR, AND COMPOSITIONS AND USE THEREOF

BACKGROUND OF THE INVENTION

1. Field of the Invention

The invention relates to a novel class of antitumor anthracycline glycosides, processes for their preparation, to pharmaceutical compositions containing them, certain novel diaminotetradeoxy sugar derivaties used in their preparation and the use thereof.

2. Prior Art

The novel compounds of the invention are derivatives of daunorubicin, a known antitumor antibiotic.

SUMMARY OF THE INVENTION

The invention provides, in one aspect thereof, a new class of anthracycline glycosides of the formula I and their pharamaceutically acceptable acid addition salts:

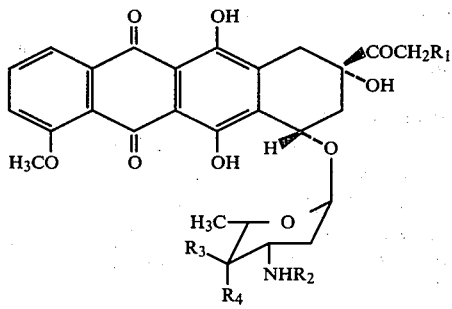

wherein $R_1$ is hydrogen or hydroxy; $R_2$ is hydrogen or an acyl group, for example, trifluoroacetyl; one of $R_3$ and $R_4$ is amino or acylamino, for example, trifluoroacetyl amino; and the other of $R_3$ and $R_4$ is hydrogen.

Among the anthracycline glycosides of the formula I are included:

4'-amino-4'-deoxy-daunorubicin (I-A) (I:$R_1=R_2=R_3=H$, $R_4=NH_2$),

4'-deoxy-4'-epi-trifluoroacetamido-daunorubicin (I-B) (I: $R_1=R_2=R_4=H$, $R_3=NHCOCF_3$), 4'-amino-4'-deoxy-4'-epi-daunorubicin (I-C) (I: $R_1=R_2=R_4=H$, $R_3=NH_2$), 4'-amino-4'-deoxy-doxorubicin (I-D) (I: $R_1=OH$, $R_2=R_3H$, $R_4=NH_2$) and 4'-amino-4'-deoxy-4'-epi-doxorubicin (I-E) (I: $R_1=OH$, $R_2=R_4=H$, $R_3=NH_2$).

The anthracycline glycosides of the formula I are useful therapeutic agents for treating certain mammalian tumors.

In another aspect the invention provides a process for the preparation of compounds of the formula I, the process comprising condensing the known aglycone daunomycinone with 2,3,4,6-tetradeoxy-3,4-ditrifluoroacetamido-L-lyxo-hexopyranosyl chloride (III-A) or with 2,3,4,6-tetradeoxy-3,4-ditrifluoroacetamido-L-arabino-hexopyranosyl chloride (III-B) to give, respectively, the protected glycosides IV-A (I: $R_1=R_3=H$, $R_2=COCF_3$, $R_4=NH-COCF_3$) and IV-B (I: $R_1=R_4=H$, $R_2=COCF_3$, $R_3=COCF_3$)

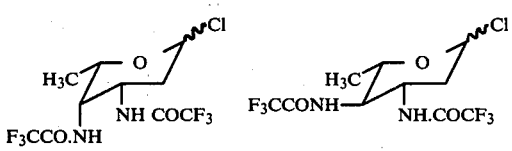

III-A   III-B and selectively removing the protecting groups to give first the daunorubicin derivatives I in which $R_2$ is trifluoroacetyl and then the daunorubicin derivatives I in which $R_2$ is hydrogen and, thereafter, optionally 14-brominating the daunorubicin derivatives and hydrolyzing the resulting 14-bromo-daunorubicin derivatives to obtain the corresponding doxorubicin derivatives. The condensation is effected in the presence of a silver salt, preferably silver trifluoromethanesulphonate, as a catalyst, according to the procedure described in U.S. Pat. No. 4,112,076. The optional bromination and hydrolysis may be effected according to the procedure described in U.S. Pat. No. 4,122,076, owned by the unrecorded assignee hereof.

In still a further aspect thereof, the invention provides certain novel intermedites used in the preparation of the anthracyclines. These intermediates are the sugars III-A and III-B, whose structures are shown above.

In yet further aspects thereof, the invention provides pharmaceutical compositions comprising a compound of the formula I or a pharmaceutically acceptable salt thereof in admixture with a pharmaceutically acceptable diluent or carrier, as well as methods of treating certain mammalian tumors with the compounds of formula I.

Finally, the novel sugars III-A and III-B are prepared from a known starting material. That starting material is methyl 2,3,6-trideoxy-3-trifluoroacetamido-α-L-threo-hexopyranosid-4-ulose (VI), a compound which is described in U.S. Pat. No. 4,039,663, owned by the unrecorded assignee hereof.

The reaction sequence by which III-A and III-B are made from VI is shown below:

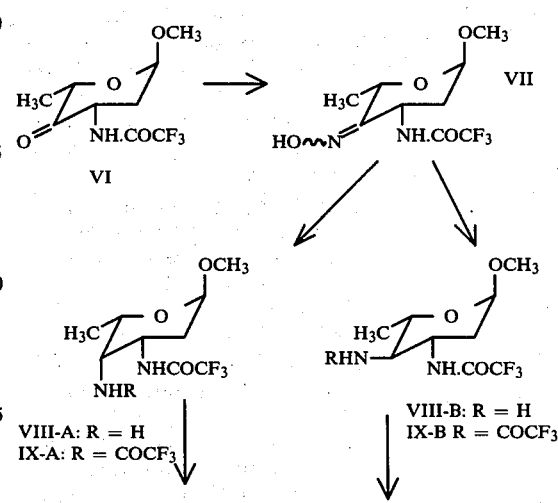

-continued

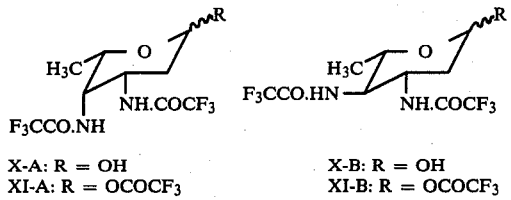

X-A: R = OH
XI-A: R = OCOCF₃

X-B: R = OH
XI-B: R = OCOCF₃

Treatment of compound VI with hydroxylamine hydrochloride in pyridine gives the oxime VII. Reduction of VII in methanol in the presence of Raney nickel as a catalyst gives a mixture of the lyxo-(VIII-A) and arabino-(VIII-B) sugar derivatives, which are separated after column chromatography. N-trifluoroacetylation followed by mild acid hydrolysis affords compound X-A and X-B respectively. Subsequent O-trifluoroacetylation and treatment with dry hydrogen chloride in anhydrous diethyl ether gives the 1-chloro derivatives III-A and III-B respectively.

DETAILED DESCRIPTION OF THE INVENTION

The invention will now be illustrated by the following Examples of the preparation of certain of the new compounds of the invention.

EXAMPLE 1

Preparation of methyl 2,3,4,6-tetradeoxy-3,4-ditrifluoroacetamido-α-L-lyxo-hexopyranoside (IX-A) and methyl 2,3,4,6-tetradeoxy-3,4-ditrifluoroacetamido-α-L-arabinohexopyranoside (IX-B)

2.5 g (1 mmol) of methyl 2,3,6-trideoxy-4-trifluoroacetamido-α-threo-hexopyranosid-4-ulose (V) were added to a solution of 4.2 g (60 mmol) of hydroxylamine hydrochloride in 20 ml of pyridine and 20 ml of methanol. The reaction mixture was stirred at room temperatue for about one hour, then diluted with 160 ml of chloroform and 100 ml of water. The organic phase was separated off, washed with water and concentrated under vacuum to give VIII, a mixture of syn- and anti-oximes, in the form of a syrup. The syrup was dissolved in 200 ml of dry methanol and hydrogenated in the presence of Raney-Nickel at 10 atmospheres for four hours. The filtered solution was evaporated to a residue and the resulting syrup was chromatographed on a silica-gel column. Elution with 2% methanol in chloroform gave a good separation of the intermediates VIII-A and VIII-B. These were N-trifluoroacetylated, in methylene dichloride with trifluoroacetic anhydride, to give respectively, methyl 2,3,4,6-tetradeoxy-3,4-ditrifluoroacetamido-α-L-lyxo-hexopyranoside (IX-A, 1.2 g, 34%) as a white solid: m.p. 118°–119° C., $[\alpha]_D^{20} -94°$ (c=1, CHCl₃), and methyl 2,3,4,6-tetradeoxy-3,4-ditrifluoroacetamido-α-L-arabino-hexopyranoside (IX-B, 1.25 g, 36%) as a white solid: m.p. 231°–232° C., $[\alpha]_D^{20} -220°$ (c=1, CHCl₃).

The structures of compound IX-A and IX-B were assigned on the basis of PMR studies in acetone-d₆ at 270 MHz. The PMR spectrum of IX-A showed absorptions at: 1.13 (d, CH₃-C-5), 3.35 (s, OCH₃), 4.22 (qd, H-C-5), 4.42 (three d, H-C-4), 4.51 (four d, H-C-3) and 4.76 δ (dd, H-C-1), while that of IX-B showed absorptions at: 1.19 (d, CH₃-C-5), 3.32 (s, OCH₃), 3.76 (three d, H-C-4) 4.02 (dq, H-C-5), 4.47 (four d, H-C-3) and 4.81 δ (dd, H-C-1).

EXAMPLE 2

Preparationof 2,3,4,6-tetradeoxy-3,4-ditrifluoroacetamido-L-lyxo-hexopyranosyl chloride (III-A].

A solution of 0.7 g (2 mmol) of compound IX-A, prepared as described in Example 1, in 20 ml of acetic acid and 45 ml of water was heated for three hours at 100° C. The reaction mixture was evaporated to a residue under vacuum to give 2,3,4,6-tetradeoxy-3,4-ditrifluoroacetamido-L-lyxo-hexose (X-A) in the form of a syrup, which was dissolved in 15 ml of methylene dichoride and treated at 0° C. with 4 ml of trifluoroacetic anhydride. After two hours at 0° C. and one hour at room temperature, the reaction mixture was evaporated to give the corresponding 1-0-trifluoroacetate (XI-A) as a syrup, which was directly dissolved in 20 ml of anhydrous diethyl ether. The solution was saturated at 0° C. with dry hydrogen chloride. After standing at 0° C. overnight, the reaction mixture was evaporated in vacuum to give the title compound suitable for the subsequent coupling reacton without further purification.

EXAMPLE 3

Preparation of 2,3,4,6-tetradeoxy-3,4-ditrifluoroacetamido-L-arabino-hexopyranosyl chloride (III-B)

Starting from methyl 2,3,4,6-tetradeoxy-3,4-ditrifluoroacetamido-L-arabino-hexopyranoside (IX-B), prepared as described in Example 1, the title compound was prepared following the procedure described in Example 2.

EXAMPLE 4

Preparation of 4'-amino-4'-deoxy-daunorubicin (I-A)

The coupling or condensation of daunomycinone (0.9 g, 2.26 mmol) in 105 ml of dry methylene dichloride with 0.645 g (1.8 mmol) of 2,3,4,6-tetradeoxy-3,4-ditrifluoroacetamido-L-lyxo-hexopyranosyl chloride (III-A), prepared as described in Example 2, in the presence of 6 of Molecular Sieve (4Å-Merck) was performed using silver trifluoromethanesulphonate (0.58 g in 15 ml of diethyl ether) as a catalyst. After one hour under vigorous stirring at room temperature, the reaction mixture was treated with a saturated aqueous solution of sodium hydrogen carbonate, and the organic phase was then separated off and evaporated under vacuum. Chromatographic purification of the crude residue on a silica-gel column using a 95:5 by volume chloroform: acetone mixture as eluent, gave 4'-trifluoroacetamido-4'-deoxy-N-trifluoroacetyl-daunorubicin (IV-A, 0.94 g, 72%): m.p. 189°–190° C. (with decomposition): $[\alpha]_D^{20} +385°$ (c=0.5, MeOH). The PMR spectrum (acetone-d₆) showed absorptions at: 1.26 (d, CH₃-C-5'), 2.40 (s, CH₃CO), 4.00 (s, CH₃-O-C-4), 5.12 (broad s, H-C-7), 5.48 (dd, H-C-1'), 12.80 and 13.70 δ (two s, phenolic OHs).

A solution of 0.36 g (0.5 mmol) of IV-A in 10 ml of acetone and 30 ml of 0.2 N aqueous sodium hydroxide was stirred under nitrogen at room temperature. After two hours the reaction mixture was acidified to pH 3.5 with aqueous hydrochloric acid and then extracted with chloroform to eliminate some impurities. The aqueous phase, adjusted to pH8, was extracted with chloroform and the extract was washed with water, dried over anhydrous sodium sulphate and concentrate to a small volume. Acidification to pH 4.5 with methanolic hydrogen chloride, followed by addition of diethyl ether, gave 4'-amino-4'-deoxy-daunorubicin (I-A, 0.21 g, 74%) as its hydrochloride: m.p. 161°-162° (with decomposition), ($[\alpha]_D^{23°}$ +252° (c=0.05 in methanol).

EXAMPLE 5

Preparation of 4'-deoxy-4'-epi-trifluoroacetamido-daunorubicin (I-B).

The coupling, or condensation of daunomycinone with 2,3,4,6-tetradexoy-3,4-ditrifluoroacetamido-L-arabino-hexopyranosyl chloride (III-B), prepared as described in Example 3, following the procedure described in Example 4, gave 4'-deoxy-4'-epi-trifluoroacetamido-N-trifluoroacetyl-daunorubicin (IV-B): m.p. 165°-166° C. (with decomposition), $[\alpha]_D^{20°}$ +145° (c=0.05, CH$_3$OH). The PMR spectrum (acetone-d$_6$) showed absorptions at 1.36 (d, CH$_3$-C-5'), 2.42 (s, COCH$_3$), 3.6–4.0(m,H-C-4'), 4.07 (s, CH$_3$-O-C-4), 5.25 (broad s, H-C-7), 5.59 (broad s, H-C-1'), 12.90 and 13.77 (two s, phenolic OHs). Treatment of IV-B (0.28 g, 0.4 mmol) in 8 ml of acetone with 24 ml of 0.2 N aqueous sodium hydroxide under nitrogen for 30 minutes at room temperature, gave, after the work-up described in Example 4, the title compound I-B (0.21 g, 85%) as its hydrochloride: m.p. 168°-169° C. (with decomposition), $[\alpha]_D^{20°}$ +213° (c=0.05, in methanol).

EXAMPLE 6

Preparation of 4'-amino-4'-deoxy-4'-epi-daunorubicin (I-C).

Removal of the trifluoracetyl protecting group from Compound I-B (prepared as described in Example 5), following the procedure described in Example 4, gave the title compound, isolated as its hydrochloride.

EXAMPLE 7

Preparation of 4'-amino-4'-deoxy-doxorubicin (I-D).

Chemical transformation of compound I-A (prepared as described in Example 4) into the title compound I-D was performed by 14-bromination followed by hydrolysis, according to the procedure described in U.S. Pat. No. 4,122,076, owned by the unrecorded assignee hereof.

BIOLOGICAL ACTIVITY

On HeLa cells cloning efficiency in vitro, the two new compounds I-A and I-B were both found to be less cytotxic than daunorubicin, as shown by the data in Table 1. In a preliminary test against P388 leukemia in mice (Table 2), both compounds were found to be much more active daunorubicin. In particular, I-A was less toxic than daunorubicin and highly active at the maximal does tested of 13.5 mg/kg.

TABLE 1

Activity on HeLa cells cloning efficiency in vitro. Treatment for 24 hours

| | Dose (ng/ml) | % of controls | ID$_{50}$ (ng/ml) |
|---|---|---|---|
| Daunorubicin[a] | 12.5 | 49–48 | 12–12 |
| | 6.2 | 73–87 | |
| | 3.1 | 88–98 | |
| XOO-O132 (I-A) | 100 | 0 | 35 |
| | 25 | 70 | |
| | 6.2 | 98 | |
| XOO-O136 (I-B) | 1600 | 0 | 180 |
| | 400 | 21 | |
| | 100 | 211 | |

[a]Data of 2 experiments

TABLE 2

Activity against P388 ascitic leukemia. Treatment i.p. on day one after tumour inoculation.

| Compound | Dose (mg/kg) | T/C % | Toxicity Deaths |
|---|---|---|---|
| Daunorubicin | 2.9 | 181 | 0/10 |
| | 4.4 | 140 | 9/10 |
| | 6.6 | 118 | 10/10 |
| XOO-O132 (I-A) | 6 | 181 | 0/10 |
| | 9 | 190 | 0/10 |
| | 13.5 | 222 | 0/10 |
| XOO-O136 (I-B) | 10 | 145 | 0/10 |
| | 20 | 154 | 0/10 |
| | 40 | 163 | 2/10 |

Variations and modifications can, of course, be made without departing from the spirit and scope of the invention.

Having thus described our invention what we desire to secure by Letters Patent and hereby claim is:

1. An anthracycline glycoside of the formula I:

(I)

[Chemical structure of anthracycline glycoside with substituents R$_1$, R$_2$, R$_3$, R$_4$, NHR$_2$, COCH$_2$R$_1$, OH, CH$_3$O, CH$_3$]

wherein R$_1$ is hydrogen or hydroxy; R$_2$ is hydrogen or trifluoroacetyl; one of R$_3$ and R$_4$ is amino or trifluoroacetylamine and the other of R$_3$ and R$_4$ is hydrogen and pharmaceutically acceptable acid addition salts thereof.

2. An anthracycline glycoside as claimed in claim 1 wherein the salt is the hydrochloride.

3. A compound according to claim 1 which is 4'-amino-4'-deoxy-daunorubicin hydrochloride.

4. A compound according to claim 1 which is 4'-deoxy-4'-epi-trifluoroacetamido-daunorubicin hydrochloride.

5. A compound according to claim 1 which is 4'-amino-4'-deoxy-4'-epi-daunorubicin hydrochloride.

6. A compound according to claim 1 which is 4'-amino-4'-deoxy-doxorubicin hydrochloride.

7. A compound according to claim 1 which is 4'-amino-4'-deoxy-4'-epi-doxorubicin hydrochloride.

8. A sugar selected from the group consisting of

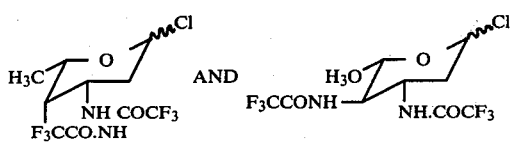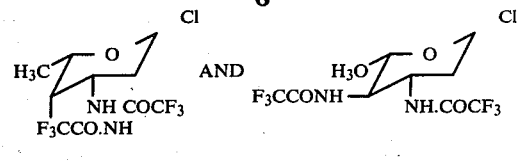

III-A   III-B

III-A   III-B

9. A pharmaceutical composition for treating P388 ascitic leukemia comprising a therapeutically effective amount of a compound according to claim 1 in combination with a carrier therefor.

10. A method of treating P388 ascitic leukemia comprising administering to a mammal afflicted therewith a therapeutically effective amount of a compound as claimed in claim 1.

UNITED STATES PATENT AND TRADEMARK OFFICE
CERTIFICATE OF CORRECTION

PATENT NO. : 4,366,149

DATED : December 28, 1982

INVENTOR(S) : Alberto Bargiotti et al

It is certified that error appears in the above-identified patent and that said Letters Patent are hereby corrected as shown below:

Title Page: left hand column, between lines 12 and 13 insert:

"Assignee: Farmitalia Carlo Erba S.p.A., Milan, Italy"

Signed and Sealed this

Fourth Day of March 1986

[SEAL]

Attest:

Attesting Officer

DONALD J. QUIGG

Commissioner of Patents and Trademarks